United States Patent [19]

Dattagupta et al.

[11] Patent Number: 4,959,309
[45] Date of Patent: * Sep. 25, 1990

[54] FAST PHOTOCHEMICAL METHOD OF LABELLING NUCLEIC ACIDS FOR DETECTION PURPOSES IN HYBRIDIZATION ASSAYS

[75] Inventors: Nanibhushan Dattagupta, New Haven; Donald M. Crothers, Northford, both of Conn.

[73] Assignee: Molecular Diagnostics, Inc., West Haven, Conn.

[*] Notice: The portion of the term of this patent subsequent to Apr. 12, 2005 has been disclaimed.

[21] Appl. No.: 107,183

[22] Filed: Oct. 9, 1987

Related U.S. Application Data

[63] Continuation of Ser. No. 611,668, May 18, 1984, Pat. No. 4,737,454, which is a continuation-in-part of Ser. No. 513,932, Jul. 14, 1983, abandoned.

[51] Int. Cl.$^5$ .................. C12Q 1/68; C07H 21/00; C07D 493/04; G01N 33/53
[52] U.S. Cl. .................................. 435/6; 435/4; 435/7; 435/18; 435/28; 435/188; 436/63; 436/94; 436/501; 436/504; 536/27; 546/109; 548/303; 935/78
[58] Field of Search .................. 435/4, 6, 7, 18, 28, 435/188; 436/63, 94, 501, 504; 536/27; 546/109; 548/303; 935/78

[56] References Cited

U.S. PATENT DOCUMENTS

| | | |
|---|---|---|
| 4,124,598 | 11/1978 | Hearst et al. |
| 4,218,539 | 8/1980 | Weltman et al. ............ 435/188 |
| 4,358,535 | 11/1982 | Falkow et al. ............ 435/6 |
| 4,486,539 | 12/1984 | Ranki et al. ............ 435/504 |
| 4,563,417 | 1/1986 | Albarella et al. ............ 435/6 |
| 4,581,333 | 4/1986 | Kourilsky et al. ............ 435/6 |
| 4,582,789 | 4/1986 | Sheldon et al. |
| 4,599,303 | 7/1986 | Yabusaki et al. ............ 435/6 |
| 4,617,261 | 10/1986 | Sheldon et al. |
| 4,737,454 | 4/1988 | Dattagupta et al. |
| 4,794,073 | 12/1988 | Dattagupta et al. ............ 536/27 X |

FOREIGN PATENT DOCUMENTS

| | | |
|---|---|---|
| 4200 | 3/1984 | Australia. |
| 7500 | 10/1984 | Australia. |
| 40310 | 10/1985 | Australia. |
| 0063879 | 11/1982 | European Pat. Off. |
| 156287 | 10/1985 | European Pat. Off. |
| 2019408 | 10/1979 | Fed. Rep. of Germany. |

OTHER PUBLICATIONS

Zeitschrift fur Naturforschung, vol. 27b, 1972, Tubingen S. Marciani, M. Terbojevic, F. Dall'Acqua "Light Scattering and Flow Dichroism Studies on DNA After the Photoreaction with Psoralen"–pp. 196–200.
Molecular & General Genetics, vol. 179, No. 1, 1980, G. Venema, U. Canosi, "The Effect of Trimethylpsoralen–Crosslinking on Entry of Donor DNA in Transformation and Transfection of Bacillus Subtilis" pp. 1-11.
Singer–Sam, J. et al, Proc. Natl. Acad. Sci., vol. 80, pp. 802–806, 1983.
Chatterjee et al, The Journal of Biological Chemistry, vol. 257, No. 15, Aug. 10, 1982, pp. 9173–9180.
Song, et al, *Annals of New York Academy of Sciences*, vol. 346, pp. 355–367, 1980.
Cantor, C. R., Annals at New York Academy Sciences, vol. 346, pp. 379–385, 1980.
Schwartz et al, Cold Spring Harbor Simposia in Quantitative Biology, vol. XLVII, pp. 189–195, 1982.
Saffran; W. et al, *Proc. Natl. Acad. Scien.*, vol. 79, pp. 4594–4598, Aug., 1982.
Transmission Electron Microscopic Method for Gene Mapping on Polytene Chromosomes by in situ Hybridization, *Proc. Natl. Acad. Sci., U.S.A.*, vol. 78, No. 11, pp. 7059–7063, Nov. 1971, Genetics.
Site–Directed Psoralen Crosslinking of DNA, Proc. Natl. Acad. Sci. U.S.A., vol. 79, pp. 4594–4598, Aug. 1982, Wilma A. Saffran, Merrill Goldenberg and Charles R. Cantor.

*Primary Examiner*—Amelia Burgess Yarbrough
*Assistant Examiner*—Ardin Marschel
*Attorney, Agent, or Firm*—Sprung Horn Kramer & Woods

[57] ABSTRACT

A labeled nucleic acid probe comprising (a) a nucleic acid component, (b) a nucleic acid-binding ligand photochemically linked to the nucleic acid component, and (c) a label chemically linked to the nucleic acid-binding ligand. The label can be a specifically bindable ligand such as a hapten or biotin, an enzyme such as a $\beta$-galactosidase or horse radish peroxidase, a fluorescent radical, a phycobiliprotein, a luminescent radical, or a radioisotope. The probe can be used in assays of nucleic acids, taking advantage of the ability of the nucleic acid component to hydridize.

36 Claims, No Drawings

FAST PHOTOCHEMICAL METHOD OF LABELLING NUCLEIC ACIDS FOR DETECTION PURPOSES IN HYBRIDIZATION ASSAYS

This is a continuation of application Ser. No. 06/611,668, filed May 18, 1984, now U.S. Pat. No. 4,737,454, which is a continuation-in-part of application No. 513,932, filed July 14, 1983, now abandoned.

The present invention relates to a photochemical method of labelling nucleic acids for detection purposes in hybridization assays for the determination of specific polynucleotide sequences.

The most efficient and sensitive method of detection of nucleic acids such as DNA after hybridization requires radioactively labelled DNA. The use of autoradiography and enzymes makes the assay time consuming and requires experienced technical people. Recently, a non-radioactive method of labelling DNA has been described by Ward et al, European Pat. Appl. 63,879; they use the method of nick translation to introduce biotinylated U residue to DNA replacing T. The biotin residue is then assayed with antibiotin antibody or an avidin containing system. The detection in this case is quicker than autoradiography but the method of nick translation is a highly skilled art. Moreover, biotinylation using biotinylated UTP works only for thymine-containing polynucleotides. Use of other nucleotide triphosphates is very difficult because the chemical derivatization of A or G or C (containing —$NH_2$) with biotin requires elaborate and highly skilled organic chemists.

It is accordingly an object of the present invention to provide a simplified system for detection of nucleic acids by hybridization assays, which system can be easily produced and used without the disadvantages noted hereinabove.

These and other objects and advantages are realized in accordance with the present invention pursuant to which the nucleic acid is labeled by means of photochemistry, employing a photoreactive nucleic acid-binding ligand, e.g., an intercalator compound such as a furocoumarin or a phenanthridine compound or a non-intercalator compound such as netropsin, distamycin, Hoechst 33258 and bis-benzimidazole to link the nucleic acid to a label which can be "read" or assayed in conventional manner, including fluorescence detection. The end product is thus a labeled nucleic acid probe comprising (a) a nucleic acid component, (b) an intercalator or other nucleic acid-binding ligand photochemically linked to the nucleic acid component, and (c) a label chemically linked to (B).

The novel photochemical method provides more favorable reaction conditions than the usual chemical coupling method for biochemically sensitive substances. By using proper wavelengths for irradiation, DNA, RNA and proteins can be modified without affecting the native structure of the polymers. The nucleic acid-binding ligand, hereinafter exemplified by an intercalator, and label can first be coupled and then photoreacted with the nucleic acid or the nucleic acid can first be photoreacted with the intercalator and then coupled to the label. A general scheme for coupling a nucleic acid, exemplified by double-stranded DNA, to a label such as a hapten or enzyme is as follows:

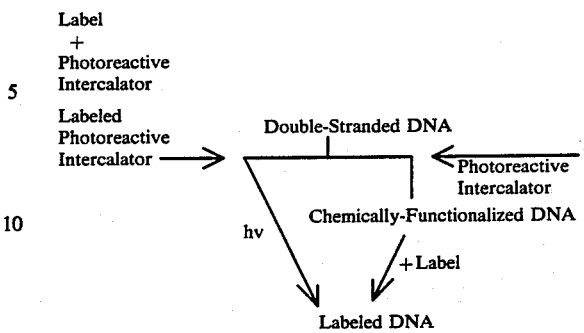

Where the hybridizable portion of the probe is in a double stranded form, such portion is then denatured to yield a hybridizable single stranded portion. Alternatively, where the labeled DNA comprises the hybridizable portion already in single stranded form, such denaturization can be avoided if desired. Alternatively, double stranded DNA can be labeled by the approach of the present invention after hybridization has occurred using a hybridization format which generates double stranded DNA only in the presence of the sequence to be detected.

To produce specific and efficient photochemical products, it is desirable that the nucleic acid component and the photoreactive intercalator compound be allowed to react in the dark in a specific manner.

For coupling to DNA, aminomethyl psoralen, aminomethyl angelicin and amino alkyl ethidium or methidium azides are particularly useful compounds. They bind to double-stranded DNA and only the complex produces photoadduct. In the case where labeled double-stranded DNA must be denatured in order to yield a hybridizable single stranded region, conditions are employed so that simultaneous interaction of two strands of DNA with a single photoadduct is prevented. It is necessary that the frequency of modification along a hybridizable single stranded portion of the probe not be so great as to substantially prevent hybridization, and accordingly there preferably will be not more than one site of modification per 25, more usually 50, and preferably 100, nucleotide bases. Angelicin derivatives are superior to psoralen compounds for monoadduct formation. If a single-stranded probe is covalently attached to some extra double-stranded DNA, use of phenanthridium and psoralen compounds is desirable since these compounds interact specifically to double-stranded DNA in the dark. The chemistry for the synthesis of the coupled reagents to modify nucleic acids for labelling, described more fully hereinbelow, is similar for all cases.

The nucleic acid component can be singly or doubly stranded DNA or RNA or fragments thereof such as are produced by restriction enzymes or even relatively short oligomers.

The nucleic acid-binding ligands of the present invention used to link the nucleic acid component to the label can be any suitable photoreactive form of known nucleic acid-binding ligands. Particularly preferred nucleic acid-binding ligands are intercalator compounds such as the furocoumarins, e.g., angelicin (isopsoralen) or psoralen or derivatives thereof which photochemically will react with nucleic acids, e.g., 4'-aminomethyl-4,5'-dimethyl angelicin, 4'-aminomethyltrioxsalen (4'-aminomethyl-4,5',8-trimethyl-psoralen, 3-carboxy-5- or -8-amino- or -hydroxy-psoralen, as well as mono- or bis-azido aminoalkyl methidium or ethidium compounds. Photoreactive forms of a variety of other intercalating agents can also be used as exemplified in the following table:

| Intercalator Classes and Representative Compounds | Literature References |
|---|---|
| A. Acridine dyes | Lerman, J. Mol. Biol. 3:18(1961); Bloomfield et al, "Physical Chemistry of Nucleic Acids", Chapter 7, pp. 429–476, Harper and Rowe, NY(1974) |
| proflavin, acridine orange, quinacrine, acriflavine | Miller et al, Biopolymers 19:2091(1980) |
| B. Phenanthridines | Bloomfield et al, supra |
| ethidium | Miller et al, supra |
| coralyne | Wilson et al, J. Med. Chem. 19:1261(1976) |
| ellipticine, ellipticine cation and derivatives | Festy et al, FEBS Letters 17:321(1971); Kohn et al, Cancer Res. 35:71(1976); LePecq et al, PNAS (USA)71: 5078(1974); Pelaprat et al, J. Med. Chem. 23:1330(1980) |
| C. Phenazines | Bloomfield et al, supra |
| 5-methylphenazine cation | |
| D. Phenothiazines | " |
| chlopromazine | |
| E. Quinolines | " |
| chloroquine | |
| quinine | |
| F. Aflatoxin | " |
| G. Polycyclic hydrocarbons and their oxirane derivatives | " |
| 3,4-benzpyrene benzopyrene diol epoxide, 1-pyrenyl-oxirane | Yang et al, Biochem. Biophys. Res. Comm. 82:929(1978) |
| benzanthracene-5,6-oxide | Amea et al, Science 176:47(1972) |
| H. Actinomycins | Bloomfield et al, supra |
| actinomycin D | |
| I. Anthracyclinones | " |
| β-rhodomycin A | |
| daunamycin | |
| J. Thiaxanthenones | " |
| miracil D | |
| K. Anthramycin | " |
| L. Mitomycin | Ogawa et al, Nucl. Acids Res., Spec. Publ. 3:79(1977); Akhtar et al, Can. J. Chem. 53:2891(2975) |
| M. Platinum Complexes | Lippard, Accts. Chem. Res. 11:211(1978) |
| N. Polyintercalators | Waring et al, Nature 252:653(1974); Wakelin, Biochem. J. 157:721(1976) |
| echinomycin | |
| quinomycin triostin BBM928A tandem | Lee et al, Biochem. J. 173:115(1978): Huang et al, Biochem. 19: 5537(1980): Viswamitra et al, Nature 289: 817(1981) |
| diacridines | LePecq et al, PNAS (USA)72:2915(1975): Carrellakis et al, Biochim. Biophys. Acta 418:277(1976); Wakelin et al, Biochem 17:5057(1978); Wakelin et al, FEBS Lett. 104:261(1979); Capelle et al, Biochem. 18:3354 (1979); Wright et al, Biochem. 19:5825(1980); Bernier et al, Biochem. J. 199:479 (1981); King et al, Biochem. 21:4982 (1982) |
| ethidium dimer | Gaugain et al, Biochem 17:5078(1978); Kuhlman et al, Nucl. Acids Res. 5:2629(1978); Marlcovits et al, Anal. Biochem. 94:259(1979); Dervan et al, JACS 100:1968(1978); al, JACS 101:3664(1979). |
| ellipticene dimers and analogs | Debarre et al, Compt. Rend. Ser. D. 284: 81(1977); Pelaprat et al, J. Med. Chem. 23:1336(1980) |
| heterodimers | Cain et al, J. Med. Chem. 21:658(1978); Gaugain et al, Biochem. 17:5078(1978) |
| trimers | Hansen et al, JCS Chem. Comm. 162(1983); Atnell et al, JACS 105:2913(1983) |
| O. Norphillin A | Loun et al, JACS 104: 3213(1982) |
| P. Fluorenes d fluorenone fluorenodiamines | Bloomfield et al, supra Witkowski et al, Wiss. Beitr.-Martin-Luther-Univ. Halle Wittenberg, 11(1981) |
| Q. Furocoumarins | |
| angelicin | Venema et al, MGG, Mol. Gen. Genet. 179;1 (1980) |
| 4,5'-dimethylangelicin | Vedaldi et al, Chem.-Biol. Interact. 36: 275(1981) |
| psoralen | Marciani et al, Z. Naturforsch B 27(2): 196(1972) |
| 8-methoxypsoralen | Belognzov et al, Mutat. Res. 84:11(1981); Scott et al, Photochem. Photobiol. 34:63(1981) |
| 5-aminomethyl-8-methoxypsoralen | Hansen et al, Tet. Lett. 22:1847(1981) |
| 4,5,8-trimethylpsoralen | Ben-Hur et al, Biochem. Biophys. Acta 331:181(1973) |
| 4'-aminomethyl-4,5,8-trimethylpsoralen | Issacs et al, Biochem. 16:1058(1977) |
| xanthotoxin | Hradecma et al, Acta Virol. (Engl. Ed.) 26: 305(1982) |
| khellin | Beaumont et al, Biochim. Biophys Acta 608:1829(1980) |
| R. Benzodipyrones | Murx et al, J. Het. Chem. 12:417(1975); Horter et al, Photochem. Photobiol. 20: 407(1974) |
| S. Monstral Fast Blue | Juarranz et al, Acta Histochem. 70:130 (1982) |

Particularly useful photoreactive forms of such intercalating agents are the azidointercalators. Their reactive nitrenes are readily generated at long wavelength ultraviolet or visible light and the nitrenes of arylazides prefer insertion reactions over their rearrangement products [see White et al, Methods in Enzymol. 46: 644

(1977)]. Representative azidointercalators are 3-azidoacridine, 9-azidoacridine, ethidium monoazide, ethidium diazide, ethidium dimer azide [Mitchell et al, JACS 104: 4265 (1982)], 4-azido-7-chloroquinoline, and 2-azidofluorene. Other useful photoreactable intercalators are the furocoumarins which form [2+2] cycloadducts with pyrimidine residues. Alkylating agents can also be used such as bis-chloroethylamines and epoxides or aziridines, e.g., aflatoxins, polycyclic hydrocarbon epoxides, mitomycin, and norphillin A.

The label which is linked to the nucleic acid component according to the present invention can be any chemical group or residue having a detectable physical or chemical property. The label will bear a functional chemical group to enable it to be chemically linked to the intercalator compound. Such labeling materials have been well developed in the field of immunoassays and in general most any label useful in such methods can be applied to the present invention. Particularly useful are enzymatically active groups, such as enzymes (see Clin. Chem. (1976) 22: 1243), enzyme substrates (see British Pat. Spec. 1,548,741), coenzymes (see U.S. Pat. Nos. 4,230,797 and 4,238,565), and enzyme inhibitors (see U.S. Pat. No. 4,134,792; fluorescers (see Clin. Chem. (1979) 25: 353) and chromophores including phycobiliproteins; luminescers such as chemiluminescers and bioluminescers (see Clin. Chem. (1979) 25: 512, and ibid, 1531); specifically bindable ligands; and residues comprising radioisotopes such as $^3H$, $^{35}S$, $^{32}P$, $^{125}I$, and $^{14}C$. Such labels are detected on the basis of their own physical properties (e.g., fluorescers, chromophores and radioisotopes) or their reactive or binding properties (e.g., enzymes, substrates, coenzymes and inhibitors). For example, a cofactor-labeled nucleic acid can be detected by adding the enzyme for which the label is a cofactor and a substrate for the enzyme. A hapten or ligand (e.g., biotin) labeled nucleic acid can be detected by adding an antibody or an antibody fragment to the hapten or a protein (e.g., avidin) which binds the ligand, tagged with a detectable molecule. Such detectable molecule can be some molecule with a measurable physical property (e.g., fluorescence or absorbance) or a participant in an enzyme reaction (e.g., see above list). For example, one can use an enzyme which acts upon a substrate to generate a product with a measurable physical property. Examples of the latter include, but are not limited to, $\beta$-galactosidase, alkaline phosphatase, papain, and peroxidase. For in situ hybridization studies, ideally the final product is water insoluble. Other labels will be evident to one of the ordinary skill in the art.

The label will be linked to the intercalator compound by direct chemical linkage such as involving covalent bonds, or by indirect linkage such as by the incorporation of the label in a microcapsule or liposome which in turn is linked to the intercalator compound. Methods by which the label is linked to the intercalator compound are essentially known in the art and any convenient method can be used to perform the present invention.

Advantageously the intercalator compound is first combined with the label chemically and thereafter combined with the nucleic acid component. For example, since biotin carries a carboxyl group it can be combined with a furocoumarin by way of amide or ester formation without interfering with the photochemical reactivity of the furocoumarin or the biological activity of the biotin, e.g.,

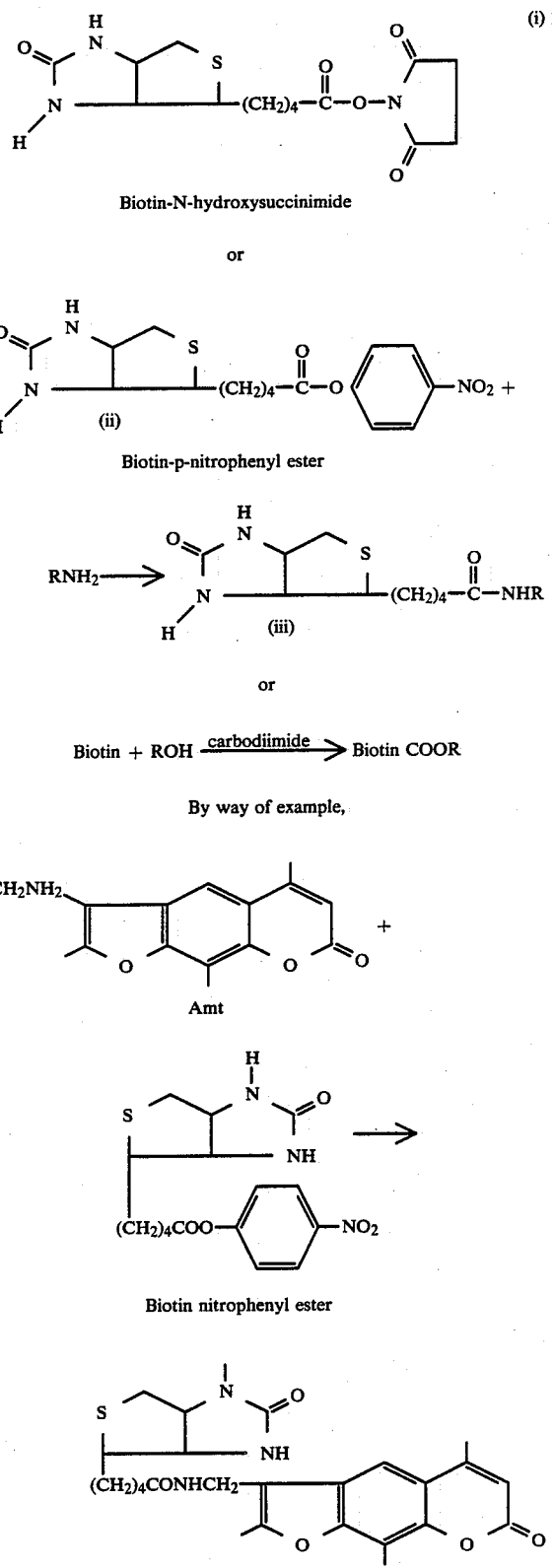

Other aminomethylangelicin, psoralen and phenanthridium derivatives can be similarly reacted, as can phenanthridium halides and derivatives thereof such as aminopropyl methidium chloride, i.e.

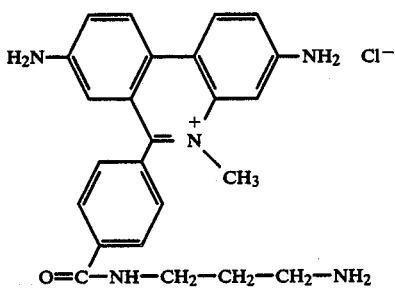

[see Hertzberg et al, J. Amer. Chem. Soc. 104: 313 (1982)]

Alternatively a bifunctional reagent such as dithiobis succinimidyl propionate or 1,4-butanediol diglycidyl ether can be used directly to couple the photochemically reactive molecule with the label where the reactants have alkyl amino residues, again in a known manner with regard to solvents, proportions and reaction conditions. Certain bifunctional reagents, possibly glutaraldehyde may not be suitable because, while they couple, they may modify the nucleic acid and thus interfere with the assay. Routine precautions can be taken to prevent such difficulties.

The particular sequence in making the labeled nucleic acid can be varied. Thus, for example, an amino-substituted psoralen can first be photometrically coupled with a nucleic acid, the product having pendant amino groups by which it can be coupled to the label. Alternatively, the psoralen can first be coupled to a label such as an enzyme and then to the nucleic acid.

The spacer chain length between the nucleic acid-binding ligand and the label can be extended via hydrocarbon or peptide. A typical example involves extending an 8-hydroxy psoralen derivative with an alkyl halide, according to the method described by J. L. DeCout and J. Lhomme, Photochemistry Photobiology, 37, 155–161 (1983). The haloalkylated derivative is then reacted either with thiol or amines to produce the reactive residue, as has been described by W. A. Saffran et al., Proc. Natl. Acad. Sci., U.S.A., 79, 4594 (1982)

If the label is an enzyme, for example, the product will ultimately be placed on a suitable medium and the extent of catalysis will be determined. Thus, if the enzyme is a phosphatase the medium could contain nitrophenyl phosphate and one would monitor the amount of nitrophenol generated by observing the color. If the enzyme is a β-galactosidase the medium can contain o-nitrophenyl-D-galacto-pyranoside which also will liberate nitrophenol.

The labeled nucleic acid of the present invention is applicable to all conventional hybridization assay formats, and in general to any format that is possible based on formation of a hybridization product or aggregate comprising the labeled nucleic acid. In particular, the unique labeled probe of the present invention can be used in solution and solid-phase hybridization formats, including, in the latter case, formats involving immobilization of either sample or probe nucleic acids and sandwich formats.

The labeled nucleic acid probe will comprise at least one single stranded base sequence substantially complementary to or homologous with the sequence to be detected. However, such base sequence need not be a single continuous polynucleotide segment, but can be comprised of two or more individual segments interrupted by nonhomologous sequences. These nonhomologous sequences can be linear or they can be self-complementary and form hairpin loops. In addition, the homologous region of the probe can be flanked at the 3'- and 5'-terminii by nonhomologous sequences, such as those comprising the DNA or RNA of a vector into which the homologous sequence had been inserted for propagation. In either instance, the probe as presented as an analytical reagent will exhibit detectable hybridization at one or more points with sample nucleic acids of interest. Linear or circular single stranded polynucleotides can be used as the probe element, with major or minor portions being duplexed with a complementary polynucleotide strand or strands, provided that the critical homologous segment or segments are in single stranded form and available for hybridization with sample DNA or RNA. Useful probes include linear or circular probes wherein the homologous probe sequence is in essentially only single stranded form [see particularly, Hu and Messing, Gene 17: 271 (1982)].

The labeled probe of the present invention can be used in any conventional hybridization technique. As improvements are made and as conceptually new formats are developed, such can be readily applied to the present labeled probe. Conventional hybridization formats which are particularly useful include those wherein the sample nucleic acids or the polynucleotide probe is immobilized on a solid support (solid-phase hybridization) and those wherein the polynucleotide species are all in solution (solution hybridization).

In solid-phase hybridization formats, one of the polynucleotide species participating in hybridization is fixed in an appropriate manner in its single stranded form to a solid support. Useful solid supports are well known in the art and include those which bind nucleic acids either covalently or non-covalently. Noncovalent supports are generally understood to involve hydrophobic bonding include naturally occurring and synthetic polymeric materials, such as nitrocellulose, derivatized nylon, and fluorinated polyhydrocarbons, in a variety of forms such as filters or solid sheets. Covalent binding supports are also useful and comprise materials having chemically reactive groups or groups, such as dichlorotriazine, diazobenzyloxymethyl, and the like, which can be activated for binding to polynucleotides.

A typical solid-phase hybridization technique begins with immobilization of sample nucleic acids onto the support in single stranded form. This initial step essentially prevents reannealing of complementary strands from the sample and can be used as a means for concentrating sample material on the support for enhanced detectability. The polynucleotide probe is then contacted with the support and hybridization detected by measurement of the label as described herein. The solid support provides a convenient means for separating labeled probe which has hybridized to the sequence to be detected from that which has not hybridized.

Another method of interest is the sandwich hybridization technique wherein one of two mutually exclusive fragments of the homologous sequence of the probe is immobilized and the other is labelled. The presence of the polynucleotide sequence of interest results in dual hybridization to the immobilized and labeled probe segments. See Methods in Enzymology 65: 468 (1980) and Gene 21: 77–85 (1983) for further details.

The invention will be further described in the following examples wherein parts are by weight unless otherwise expressed.

EXAMPLE 1

50 mg of N-hydroxysuccinimido biotin is dissolved in 2 ml dimethylsulfoxide (soln A). 10 mg of 4' aminomethyl trioxsalen (structure 1) (or other aminoalkyl compounds) is dissolved in 10 ml (soln B) aqueous buffer (e.g., 10 mM sodium tetraborate, pH adjusted with HCl) solution pH~8. Solution (A) and (B) are mixed in a volume ratio of 1:10 and weight ratio of 10:1, so that the activated hapten is present in large excess. The reaction is allowed to proceed at 35° C. for 1 hour. The extent of the reaction is monitored by thin layer chromatography—on silica gel plates with a fluorescence indicators n a solvent 1/1/8—methanol/Acetic acid/chloroform. Under these TLC conditions unreacted aminomethyl trioxalane moves with the solvent front whereas the product has a slower mobility. Biotin does not show any fluorescence but the adduct fluoreces because of trioxsalen. Growth of the new fluorescent spot and disappearance of the original fluorescent spot indicates the extent of product formation. Since the activated biotin is in large excess, fluorescence corresponding to the starting material vanishes on TLC after the completion of reaction. Excess active biotin is reacted with glycyl-glycine or lysine. The presence of amino acid biotin product does not interfere with the photochemical reaction of psoralen-biotin compounds with DNA. Hence, a purification step after the above reaction is not essential.

EXAMPLE 2

100 mg of biotin nitrophenyl ester is dissolved in dry DMSO (2-5 ml) and 10 mg of 4'-aminomethyl trioxsalen is dissolved in dry DMSO (5 ml). The two solutions are mixed in a molar ratio so that biotin nitrophenyl ester is about ten times with respect to 4'-aminomethyl trioxsalen. 100 ml of triethylamine is added to the mixture and shaken well. The progress of reaction is checked by TLC and excess unreacted biotin nitrophenyl ester is reacted with lysine as in Example 1. The reaction is allowed to proceed for 1 hour at 35° C. and then lysine is added to quench the reaction. After the reaction, DMSO is evaporated under vacuum and the gummy residue is taken in methanol and can be chromatographically purified on an LH 20 column, using methanol as an eluant. The last step is not essential for the photochemical interaction of psoralen adduct with DNA.

EXAMPLE 3

Biotin can be coupled to aminoalkyl hydroxyalkyl compounds by carbodiimide mediated reaction. 10 mg biotin is dissolved in 1 ml dimethyl formamide. To the solution, 5 mg of 4'-hydroxymethyl trioxsalen is added followed by 10 mg dicyclohexyl carbodiimide. The reaction is allowed to proceed for 20 hours at room temperature, dicyclohexylurea precipitate is removed and the product is recovered by removing DMF under vacuum. The same reaction can be performed in pyridine.

The foregoing examples will be give similar results if the animoalkyl trioxsalen is replaced by other aminoalkyl furocoumarins, phenanthridium halides, and the like.

EXAMPLE 4

Coupling of an Enzyme to a Photoactive Amino Compound and then Covalent Attachment to DNA A typical example is given with papain. 0.1 mg/ml of papain solution in 100 mM phosphate buffer (pH 8) is added to 10 mg/ml of amino methyl trioxsalen. The final solution should be 1:1 with respect to volume of enzyme and photoactivator solution. Then solid dithiobis-succinimidyl propionate or dimethyl suberimidate added to a final concentration of 20 µg/ml. The pH is continuously monitored and maintained at the original value by 0.001M sodium hydroxide. After adding the crosslinker twice, the reaction is allowed to proceed for 30 minutes at room temperature. The free photoactive amine is separated from the enzyme-bound compounds by gel filtration on Sephadex G-10. The adduct is excluded along with the free protein and protein-protein conjugates. Most of these impurities have very little effect on DNA binding. Any enzyme which has been modified and still retains its activity can be coupled similarly.

After the purification, the enzyme conjugate is mixed with DNT in aqueous buffer (pH 7.5) and irradiated at 390 nm for 1 hour. The adduct is separated from the unreacted residues on Sephadex (G-100) column. The activity is tested as follows: DNA-enzyme conjugate is dialyzed against 10 mM EDTA-containing buffer (pH 6.2). To 8 ml of the DNA-enzyme solution, 10 ml of 60 mM mercaptoethanol and 1 ml 50 m mol cysteine (freshly prepared) are added. This is treated as enzyme solution. The substrate solution is prepared as follows: 592 mg benzoyl-L-arginine ethyl ester hydrochloride is dissolved in 30 ml water (BAEE). To this BAEE solution, 1.6 ml 0.01M EDTA, 1.6 ml 0.05M cysteine, freshly prepared are added, pH is adjusted at 6.2 and the final volume is made up to 42 ml.

PROCEDURE

Using a pH meter, the following test system has been set up at 25° C.:
 5 ml substrate
 5 ml H$_2$O
 5 ml 3M NaCl
 1 ml enzyme dilution
The amount of 0.01M NaOH in ml required to maintain a pH of 6.2 is recorded. A five-minute period is generally satisfactory.

Since enzyme are not stable at higher temperatures, if the conjugates are used for hybridization assays, low temperatures should be used. (Either oligonucleotides, or an ionic strength less than 2 m molar should be utilized so that hybridization can be effected at low temperature.

EXAMPLE 5

Identical products are generated if aminoalkyl-photoactive compounds are photoreacted with DNA first, then with the proteins or enzymes or haptens. DNA (1 mg/ml) and amino methyl trioxsalen (0.1 mg/ml) are mixed in aqueous buffer pH (7.5), and photoirradiated at 390 nm for 1 hour; the product is precipitated with ethanol then redissolved in crosslinking buffer as in Example 4, and the rest of the procedure is similar.

If monoadduct formation is essential, monoazidoaminopropyl methidium or aminomethyl angelicin compounds are used under otherwise identical conditions.

EXAMPLE 6

A glycoprotein can be coupled by redox reaction to an aliphatic amine. A typical example is given below with horse radish peroxidase (HRPO) coupling to 4' aminomethyl trioxsalen. Identical conditions can be followed with any aminoalkyl compound.

Scheme

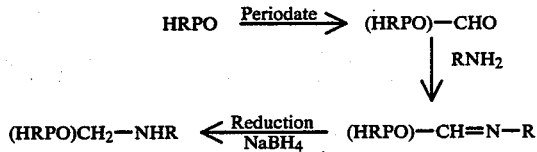

Experiment 10 mg HRPO (Sigma Chemical Co.) is dissolved in 2 ml freshly prepared 0.3M sodium bicarbonate (pH 8.1). To the enzyme solution, 200 microliter 1% 2,4-dinitrofluorobenzene in ethanol is added to block $\alpha$- and $\epsilon$- amino groups and some hydroxy groups of the enzyme. The mixture is gently shaken for one hour at room temperature. Then 2 ml 80 m molar sodium periodate in distilled water is added and mixed for 30 minutes at room temperature. In order to quench the unreacted periodate, ethylene glycol is added to a final concentration of 50 m Mol. The solution is dialyzed against 10 m molar sodium carbonate buffer (pH 9.5) in a cold room ($\sim 4°$ C.). To the dialyzed solution, $\sim 1$ mg solid aminomethyl trioxsalen is added and the mixture is shaken gently for 1 hour at 25° C. 10 mg sodium borohydride ($NaBH_4$) solid is added and the reaction is allowed to proceed for 12 hours at 4° C. The adduct is dialyzed against the DNA binding buffer and then photoreacted by mixing in 1:1 weight ratio (enzyme to DNA) as described before. The separation of the DNA-enzyme adduct from the enzyme is done by gel filtration on a Sephadex G-100 column where the adduct is excluded.

To improve the photochemical efficiency, blocking of reactive HRPO sites before oxidation with periodate may be done with allylisothiocyanate, as has been described by P. K. Nakane et al, Enzyme Labeled Antibodies for Light and Electron Microscopic Localization of cigens, J. Histochem Cytocil, 14, 790 (1966).

Unless stated otherwise, all the reactions are performed in the dark or red light conditions are maintained.

The peroxidase activity is measured by the following method:

100–500 microliters of the sample are mixed with 3 ml 14 mM para-Cresol in 50 m molar tris HCl buffer (pH 7.5). To this 1 ml 1% $H_2O_2$ is added. After 2 minutes, 3 ml 5 m molar sodium cyanides in water are added to quench the reaction. The fluorescence of the solution is measured at excitation 320 nm, emission 410 nm. H. Perschke and E. Broda, Nature 190, 257 (1961); M. Roth, Methods of Biochemical Analysis, vol. 17, ed. D. Glick, Interscience Publisher, N.Y., 1969, P. 236.

EXAMPLE 7

Assay for the Label After DNA-DNA Hybridization

An illustrative example with a single stage DNA-DNA hybridzation is presented here. The procedure used in the case of two-stage hydribization (Application Ser. No. 511,063, filed July 5, 1983 now pending) can also be followed.

In application Ser. No. 511,063 there is disclosed a method for determining whether the nucleic acid in a test sample includes a particular neucleic acid sequence, comprising the steps of:

(a) extracting the nucleic acids from a test sample, (b) digesting the extracted nucleic acids with a restriction enzyme thereby to effect restriction or not to effect restriction, depending on whether or not the restriction enzyme recognition site is precisely present in a sequence in the test DNA, (c) treating the product of (b) to form single-stranded nucleic acids, (d) contacting the single-stranded nucleic acids produced in (c) with first and second polynucleotide probes which are complementary to respective first and second portions of the sequence to be detected, the two portions being non-overlapping and immediately adjacent to the restriction site in question, and such contact being performed under conditions favorable to hybridization of said first and second probes to the sequence to be detected, hybridization with both of the probes to a test molecule being dependent upon whether in step (b) restriction did not occur, the first probe being incorporated with a distinguishable label, (e) separating, by means of the second probe, (i) any resulting dual hybridization product comprising the sequence to be detected hybridized to both the labeled first probe and the second probe, from (ii) any unhybridized and singly hybridized labeled first probe, and (f) by means of said label detecting any of the separated dual hybridization product which may be present. Plasmid pBR322 (New England Biolab) is digested with the restriction endonuclease, Pst 1 and Pvu 1. This double digestion produces one fragment of 126 base pair long DNA containing the part of ampicillin resistance gene and another fragment of 4236 base pair long DNA. The 126 bp long fragment is isolated by running the double digest on 5% polyacrylamide gel. A part of this DNA is labeled either with biotin or with enzymes as described before and used as the labeled probe. For hybridization, Pst 1 cut pBR322 (for control) or the test sample DNA is covalently linked to cellulose by photochemical method (Application Ser. No. 511,064, filed July 5, 1983 now U.S. Pat. No. 4,542,102, issued Sept. 17, 1985), by cyanogen bromide activation or by diazotization method (H. Bünemann, Nucleic Acids Res., 10, 7181 (1982)).

The cellulose containing the denatured DNA is suspended in 5 m molar salt solution for hybridization with enzyme-coupled DNA or suspended in 2.4M tetraethylammonium chloride when biotinylated DNA is used. Then hybridization is done as described by H. Bünemann in Nucleic Acids Research, 10, 7181 (1982) for the detection of the ampicillin resistance gene using 126 base pairs labeled fragment as the probe. In low salt, hybridization is done at 30°–40° C.; in 2.4M (high salt), it is done between 40° and 50° C.

After hybridization, FITC-labelled avidine is used to assay for biotin or proper enzyme assay is done with the particles.

It will be understood that the specification and examples are illustrative but not limitative of the present invention and that other embodiments within the spirit and scope of the invention will suggest themselves to those skilled in the art.

What is claimed is:

1. A labeled hydribizable nucleic acid comprising (a) a nucleic acid component, (b) a nucleic acid-binding ligand photochemically linked to the nucleic acid component thereby modifying the nucleic acid such that the frequency of modification along a hybridizable single stranded portion of the nucleic acid not be so great as to substantially prevent hybridization, and (c) a label chemically linked to (b), said label selected from the group consisting of fluorescein and phycobiliprotein.

2. A hydridizable labeled nucleic acid according to claim 1, wherein the nucleic acid-binding ligand is an intercalator compound selected from the group consisting of acridine dyes, phenanthridines, phenazines, furocoumarins, phenothiazines and quinolines.

3. A hybridizable labeled nucleic acid according to claim 2, wherein the intercalator compound is a furocoumarin or a phenanthridine.

4. A hybridizable labeled nucleic acid according to claim 1, wherein the label is fluorescein.

5. A hybridizable labeled nucleic acid according to claim 1, wherein the label is a phycobiliprotein.

6. A hybridizable labeled nucleic acid according to claim 1, wherein (b) is a radical of an amino-substituted angelicin or psoralen.

7. A hybridizable labeled nucleic acid according to claim 1, wherein the nucleic acid component is in single stranded form.

8. An adduct suitable for photochemical attachment to a hybridizable nucleic acid probe, comprising a nucleic acid-binding ligand and a label chemically linked thereto, whereby linkage of the adduct to the nucleic acid modifies the nucleic acid such that the frequency of modification along a hybridizable single stranded portion of the nucleic acid not be so great as to substantially prevent hybridization, wherein the adduct is capable of being photochemically linked to the nucleic acid and wherein the label is selected from the group consisting of fluorescein and phycoiliprotein.

9. An adduct according to claim 8, wherein the nucleic acid-binding ligand is an intercalator compound selected from the group consisting of acridine dyes, phenanthridines, phenazines, furocoumarins, phenothiazines and quinolines.

10. An adduct according to claim 9, wherein the intercalator compound is a furocoumarin or a phenanthridine.

11. An adduct according to claim 8, wherein the label is fluorescein.

12. An adduct according to claim 8, wherein the label is a phycobiliprotein.

13. An adduct according to claim 8, wherein the nucleic acid-binding ligand is an angelicin or psoralen carrying an amino substituent.

14. A method for determining a particular polynucleotide sequence in a test sample, comprising the step of:
(a) combining the test sample with a polynucleotide probe having a base sequence substantially complementary to the sequence to be determined, wherein a mono-adduct forming nucleic acid-binding ligand is photochemically linked to a sequence selected from the group consisting of the sample sequence and the probe sequence, the nucleic acid-binding ligand being chemically linked to a detectable label moiety, wherein the label is selected from the group consisting of fluorescein and phycobiliprotein, and
(b) detecting the formation of hybrids between the sample sequence to be determined and the probe sequence by measuring said detectable label moiety.

15. A method according to claim 14, wherein the nucleic acid-binding ligand is an intercalator compound selected from the group consisting of acridine dyes, phenanthridines, phenazines, furocoumarins, phenothiazines and quinolines.

16. A method according to claim 15, wherein the intercalator compound is a furocoumarin or a phenanthridine.

17. A method according to claim 14, wherein the label is fluorescein.

18. A method according to claim 14, wherein said probe sequence is a first probe sequence and is labeled and an immobilized form of a second probe sequence is combined with the test sample, the first and second probe sequences being complementary to mutually exclusive portions of the sample sequence to be determined.

19. A labeled hybridizale nucleic acid according to claim 11, wherein the linker group is selected from the group consisting of dithiobis succinimidyl propionate and 1,4-butanediol diglycidyl ether.

20. An adduct suitable for photochemical attachment to a nucleic acid comprising
(a) a nucleic acid-binding ligand,
(b) a linker group coupled to the nucleic acid-binding ligand and
(c) a label chemically linked through the linker group to the nucleic acid-binding ligand, whereby linkage of the adduct to the nucleic acid modifies the nucleic acid such that the frequency of modification along a hybridizable single stranded portion of the nucleic acid not be so great as to substantially prevent hybridization, wherein the adduct is capable of being photochemically linked to the nucleic acid and wherein the label is selected from the group consisting of fluorescein and phycobiliprotein.

21. An adduct according to claim 20, wherein the linker group is selected from the group consisting of dithiobis succinimidyl propionate and 1,4-butanediol diglycidyl ether.

22. A hybridizable labeled nucleic acid comprising (a) a nucleic acid component, (b) a nucleic acid-binding ligand photochemically linked to the nucleic acid component thereby modifying the nucleic acid such that the frequency of modification along a hybridizable single stranded portion of the nucleic acid not be so great as to substantially prevent hydridization, and (c) a label chemically linked to (b), wherein the nucleic acid is modified at not more than one site per 50 nucleotide bases.

23. A hybridizable labeled nucleic acid comprising (a) a nucleic acid component, (b) a nucleic acid-binding ligand photochemically linked to the nucleic acid component thereby modifying the nucleic acid such that the frequency of modification along a hybridizable single stranded portion of the nucleic acid not be so great as to substantially prevent hybridization, and (c) a label chemically linked to (b), wherein the nucleic acid is modified at not more than one site per 100 nucleotide bases.

24. A method of making a labeled nucleic acid probe, which comprises contacting such probe with an adduct according to claim 8 and subjecting the probe and adduct to photochemical irradiation, wherein the nucleic acid is modified at not more than one site per 50 nucleotide bases.

25. A method of making a labeled nucleic acid probe, which comprises contacting such probe with an adduct according to claim 8 and subjected the probe and adduct to photochemical irradiation, wherein the nucleic acid is modified at not more than one site per 100 nucleotide bases.

26. A labeled hybridizable nucleic acid comprising
(a) a nucleic acid component,
(b) a nucleic acid-binding ligand photochemically linked to the nucleic acid component thereby modifying the nucleic acid such that the frequency of modification along a hybridizable single stranded portion of the nucleic acid not to be so great as to substantially prevent hybridization,
(c) a linker group coupled to the nucleic acid-binding ligand and
(d) a label chemically linked through the linker group to the nucleic acid-binding ligand, wherein the nucleic acid is modified at not more than one site per 50 nucleotide bases.

27. A labeled hybridizable nucleic acid comprising
(a) a nucleic acid component,
(b) a nucleic acid-binding ligand photochemically linked to the nucleic acid component thereby modifying the nucleic acid such that the frequency of modification along a hybridizable single stranded portion of the nucleic acid not to be so great as to substantially prevent hybridization,
(c) a linker group coupled to the nucleic acid-binding ligand and
(d) a label chemically linked through the linker group to the nucleic acid binding ligand, wherein the nucleic acid is modified at not more than one site per 100 nucleotide bases.

28. A labeled hybridizable nucleic acid comprising
(a) a nucleic acid component,
(b) an intercalator compound photochemically linked to the nucleic acid component thereby modifying the nucleic acid such that the frequency of modification along a hybridizable single stranded portion of the nucleic acid not be so great as to substantially prevent hybridization, and
(c) a label chemically linked to (b), the labeled hybridizable nucleic acid produced by a process of
 (i) photochemically linking the nucleic acid component to the intercalator compound and chemically linking a label to a photochemically linked intercalator compound, or
 (ii) chemically linking a label to the intercalator compound to form a composite and photochemically linking said composite to the nucleic acid component, wherein the nucleic acid is modified at not more than one site per 50 nucleotide bases.

29. A labeled hybridizable nucleic acid comprising
(a) a nucleic acid component,
(b) an intercalator compound photochemically linked to the nucleic acid component thereby modifying the nucleic acid such that the frequency of modification along a hybridizable single stranded portion of the nucleic acid not be so great as to substantially prevent hybridization, and
(c) a label chemically linked to (b), the labeled hybridizable nucleic acid produced by a process of
 (i) photochemically linking the nucleic acid component to the intercalator compound and chemically linking a label to a photochemically linked intercalator compound, or
 (ii) chemically linking a label to the intercalator compound to form a composite and photochemically linking said composite to the nucleic acid component, wherein the nucleic acid is modified at not more than one site per 100 nucleotide bases.

30. A kit for determining a particular polynucleotide sequence in a test sample, comprising in one or more containers
(a) a polynucleotide probe having a base sequence complementary to the sequence to be determined and
(b) a mono-adduct forming nucleic acid-binding ligand being chemically linked to a detectable label moiety, said ligand being photochemically linked to the probe or being capable of being photochemically linked to the sample, wherein the label is selected from the group consisting of fluorescein and phycobiliprotein.

31. A kit according to claim 30, wherein the nucleic acid-binding ligand is an intercalator compound selected from the group consisting of acridine dyes, phenanthridines, phenazines, furocoumarins, phenothiazines and quinolines.

32. A kit according to claim 31, wherein the intercalator compound is a furocoumarin or a phenanthridine.

33. A kit according to claim 30, wherein the label is fluorescein.

34. A kit according to claim 30, wherein the label is phycobiliprotein.

35. A method according to claim 14, wherein the label is phycobiliprotein.

36. A labeled hybridizable nucleic acid according to claim 27, wherein the linker group is selected from the group consisting of dithiobis succinimidyl propionate and 1,4-butanediol diglycidyl ether.

* * * * *